United States Patent [19]

Gibson

[11] Patent Number: 5,046,489

[45] Date of Patent: Sep. 10, 1991

[54] PROSTHETIC DEVICE

[76] Inventor: Greg Gibson, 474 Mount Vernon, Council Bluffs, Iowa 51503

[21] Appl. No.: 629,396

[22] Filed: Dec. 18, 1990

[51] Int. Cl.⁵ .......................... A61F 2/50; A61F 5/41
[52] U.S. Cl. ..................... 128/79; 128/844; 604/347
[58] Field of Search ............... 128/79, 844; 604/347, 604/348, 349, 350, 351, 352, 353

[56] References Cited

U.S. PATENT DOCUMENTS

| | | | |
|---|---|---|---|
| 2,348,773 | 5/1944 | Wyman | 604/349 |
| 2,358,440 | 9/1944 | Bowman | 128/844 |
| 2,567,926 | 9/1951 | Dunkelberger | 128/844 |
| 3,037,508 | 6/1962 | Friedman | 128/844 |
| 3,683,901 | 8/1972 | Wegener | 128/79 |
| 3,820,533 | 6/1974 | Jones | 128/79 |
| 4,022,196 | 5/1977 | Clinton | 128/79 |
| 4,281,648 | 8/1981 | Rogers | 128/79 |
| 4,432,357 | 2/1984 | Pomeranz | 128/79 |
| 4,498,466 | 2/1985 | Pomeranz | 128/79 |
| 4,564,006 | 1/1986 | Pomeranz | 128/79 |
| 4,798,600 | 1/1989 | Meadows | 128/844 |
| 4,966,166 | 10/1990 | Leffler | 128/844 |

Primary Examiner—Paul J. Hirsch
Attorney, Agent, or Firm—Zarley McKee Thomte Voorhees & Sease

[57] ABSTRACT

A prosthetic apparatus includes a conventional condom having elastic characteristics, with an elastic band tightly wrapped around the condom between the closed tip end and the open end. The elastic band forms a fluid-sealed chamber in the tip end of the condom into which fluid is placed so as to expand the tip end of the condom. The method for utilizing the prosthetic apparatus includes the initial step of tightly wrapping an elastic band around a rigid sleeve. A hollow tube is then inserted into a condom and then inserted through the rigid sleeve such that the tip end of the condom and tube project out the end thereof. The elastic band is then moved from the sleeve onto the condom and the sleeve is removed. The condom is then applied to a body member and fluid is injected through the tube into the fluid-sealed chamber formed by the elastic band on the condom. The tube is then removed from the condom.

5 Claims, 3 Drawing Sheets

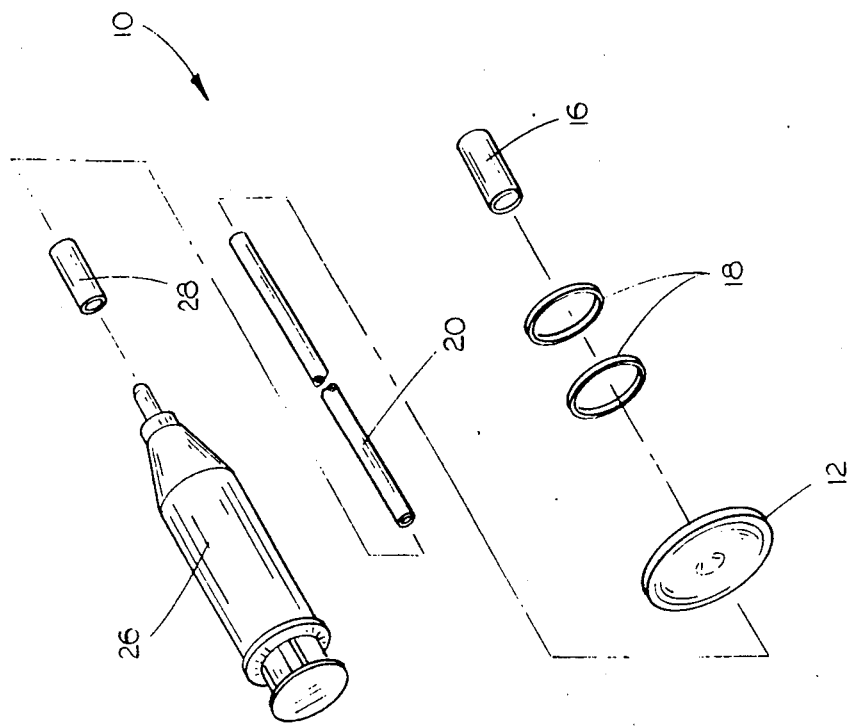
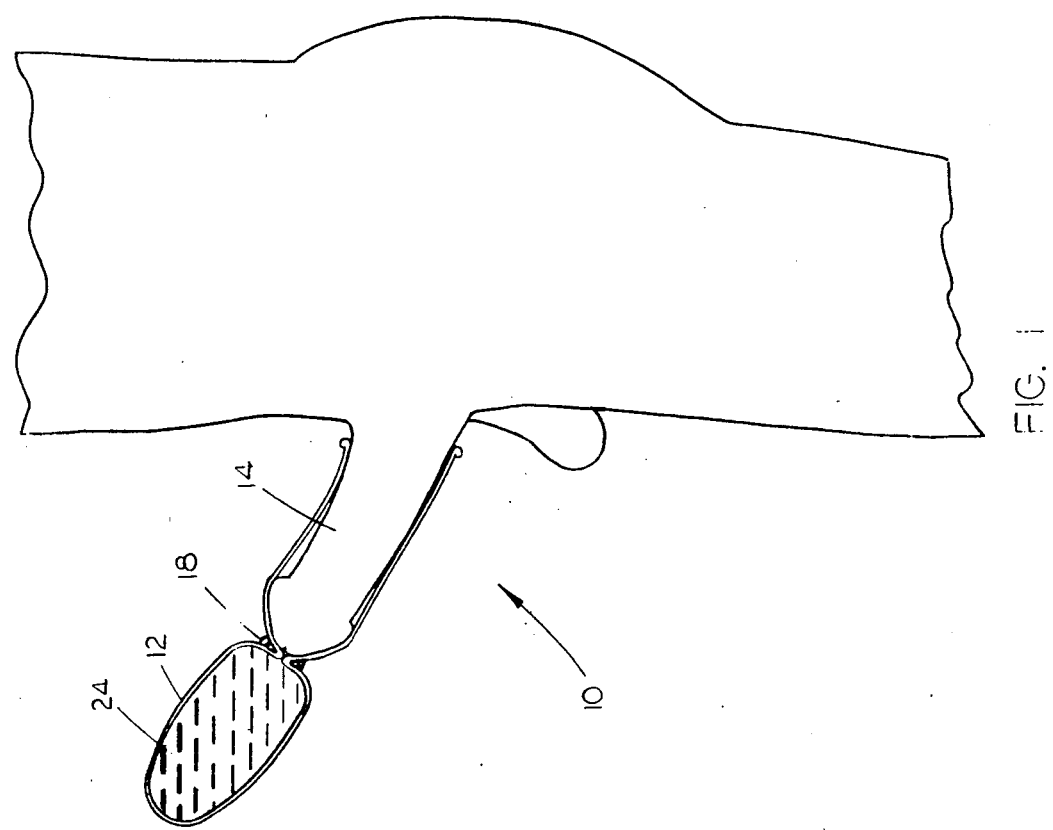

PROSTHETIC DEVICE

TECHNICAL FIELD

The present invention relates generally to prosthetic devices, and more particularly to a prosthetic device utilizing a conventional prophylactic or condom.

BACKGROUND OF THE INVENTION

Contraceptives have been known for some time, and serve to prevent conception as well as to prevent the spread of disease. Several prosthetic apparatus of the prior art also recognize the need for a prosthetic device for the purpose of elongating the male sex organ artificially to facilitate mutually satisfactory sexual relations. The male sex organ may be inadequate for a number of reasons, and therefore in order to accommodate his partner, and enhance sexual relations, a prosthetic device may be needed.

It is therefore a general object of the present invention to provide an improved prosthetic device and method of use.

Another object of the present invention is to provide a method of using a conventional condom to create a prosthetic apparatus.

A further object of the present invention is to provide a prosthetic apparatus which is simple to utilize.

Yet another object is to provide a prosthetic apparatus which may be utilized more than once with conventional condoms.

These and other objects will be apparent to those skilled in the art.

SUMMARY OF THE INVENTION

The prosthetic apparatus of the present invention includes a conventional condom having elastic characteristics, with an elastic band tightly wrapped around the condom between the closed tip end and the open end. The elastic band forms a fluid-sealed chamber in the tip end of the condom into which fluid is placed so as to expand the tip end of the condom. The method for utilizing the prosthetic apparatus includes the initial step of tightly wrapping an elastic band around a rigid sleeve. A hollow tube is then inserted into a condom and then inserted through the rigid sleeve such that the tip end of the condom and tube project out the end thereof. The elastic band is then moved from the sleeve onto the condom and the sleeve is removed. The condom is then applied to a body member and fluid is injected through the tube into the fluid-sealed chamber formed by the elastic band on the condom. The tube is then removed from the condom.

BRIEF DESCRIPTION OF THE DRAWINGS

FIG. 1 is a sectional view of the prosthetic apparatus of the present invention in place on a person;

FIG. 2 is an exploded perspective view of the various components of the prosthetic apparatus;

DESCRIPTION OF THE PREFERRED EMBODIMENT

Figure 3:
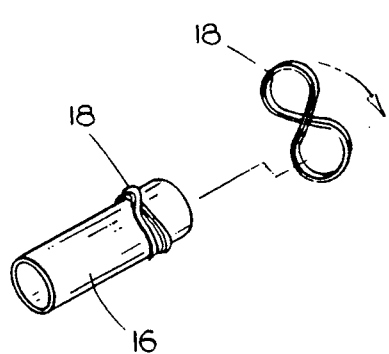
FIG. 3 is a perspective view of the first step in utilizing the method of this invention.

Referring now to the drawings, in which identical or corresponding parts are identified with the same reference numeral, and more particularly to FIG. 1, the prosthetic apparatus of the present invention is designated generally at 10 and includes a conventional condom 12 adapted for use on the male penis 14.

Figure 4:
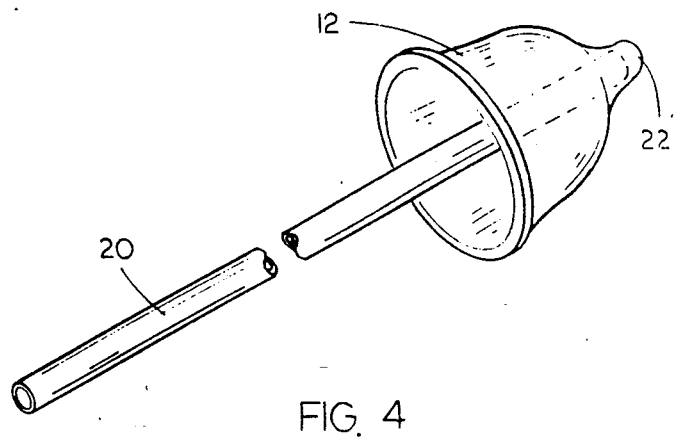
FIG. 4 is a perspective view of the components utilized in the second step in the method of use of this invention.

Referring now to FIG. 3, the first step in utilizing the prosthetic apparatus requires a short rigid sleeve 16 and a pair of rubber bands 18. Each rubber band 18 is twisted so as to be as tight as possible and wrapped on one end of sleeve 16. Referring to FIG. 4, a length of flexible small diameter tubing 20 is positioned with one end inserted within the tip 22 of a partially unrolled condom 12. Preferably, sleeve 16 is approximately one inch long, and approximately a two-inch length of condom is unrolled for the step of FIG. 4.

Figure 5:
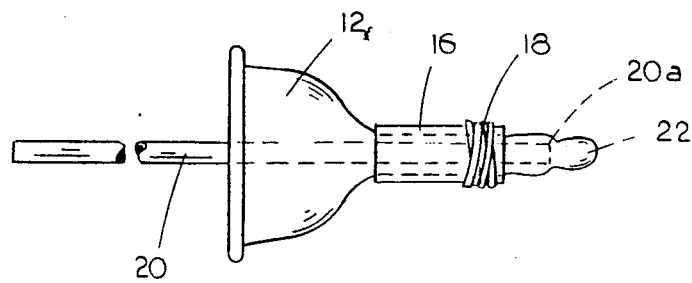
FIG. 5 is a side elevational view of the components utilized in the third step of the method.
Figure 6:
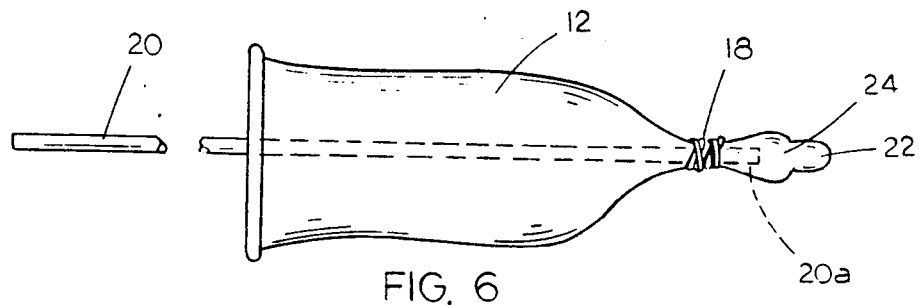
FIG. 6 is a side elevational view of the fourth step in the method of use of the invention.

As shown in FIG. 5, the condom tip 22 is inserted through sleeve 16 and pushed therethrough utilizing tube 20 until approximately an inch of the condom 12 projects out the opposite end of sleeve 16. It is important that the forward end 20a of tube 20 project beyond sleeve 16, preferably about ⅜ of an inch. Rubber bands 18 are then rolled or pushed off the end of sleeve 16 so as to tightly engage the condom 12 on the end of tubing 20a. The condom 12 may then be completely unrolled, as shown in FIG. 6, and sleeve 16 removed therefrom. The tip of the condom 22 forms a resiliently expandable portion 24 sealed by rubber bands 18 on tube 20.

Figure 7:
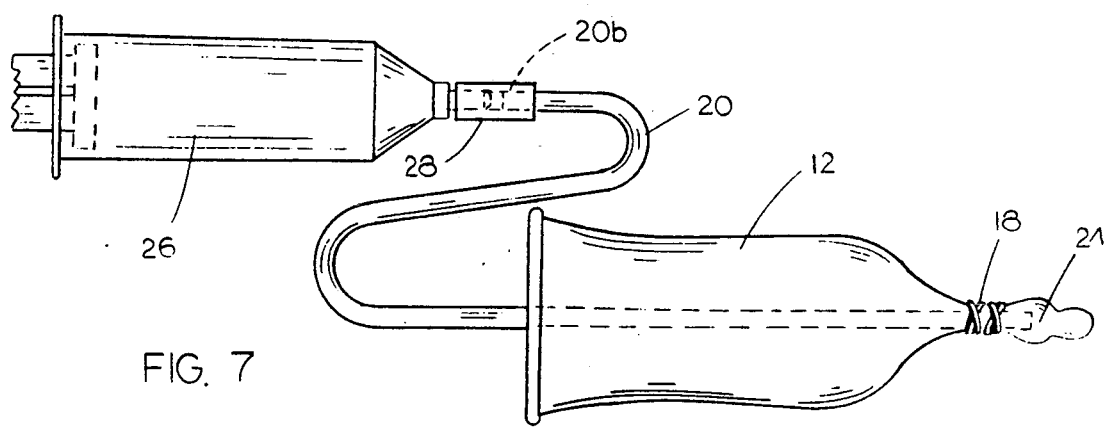
FIG. 7 is a side elevational view of the fifth step in the use of the invention.

Referring now to FIG. 7, a syringe 26 is connected to the opposite end 20b of tube 20 utilizing and adapter 28 or the like. Preferably, syringe 26 is filled with warm water or other liquid.

Figure 9:
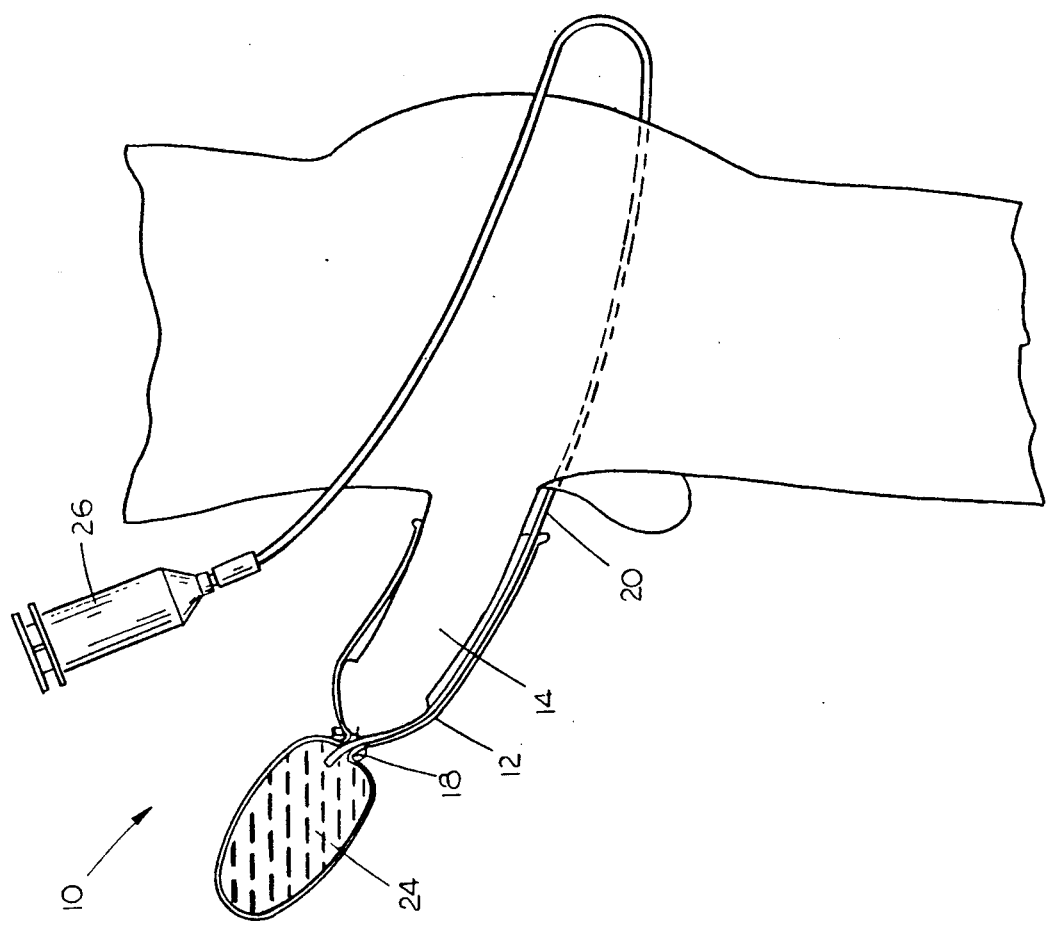
FIG. 9 is a partial sectional view showing the seventh step in the method of use of the invention.
Figure 8:
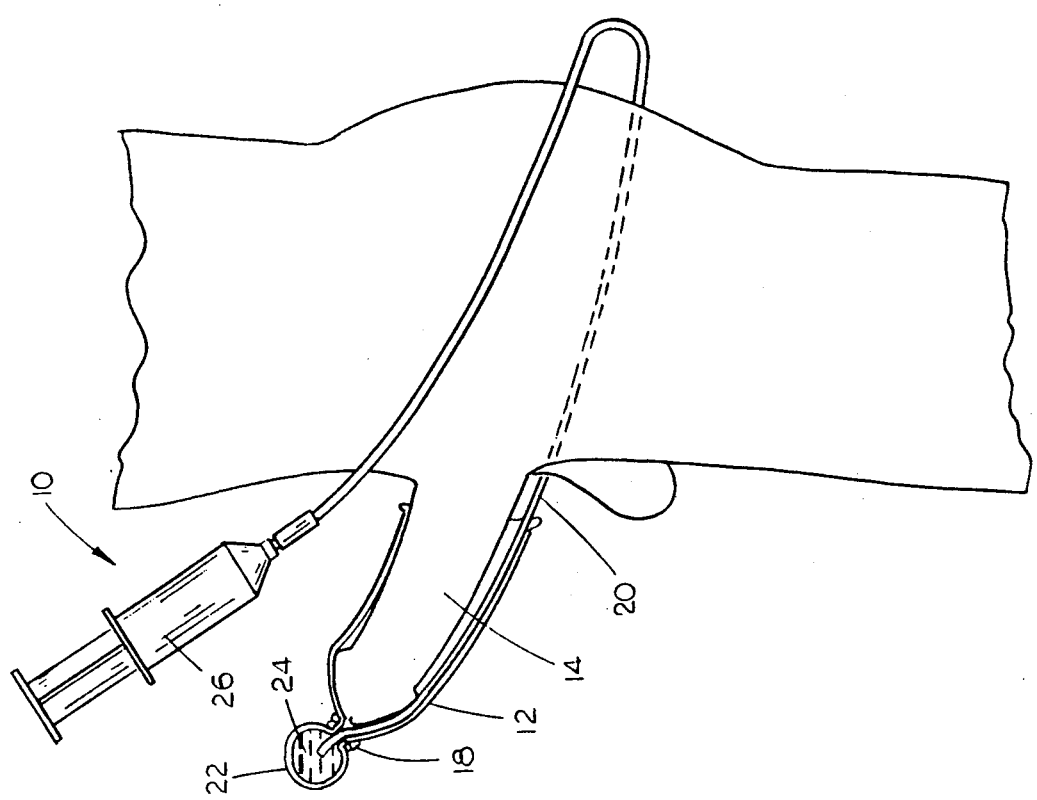
FIG. 8 is a partial sectional view showing the sixth step in the method of use of the invention.

Referring now to FIGS. 8 and 9, the prosthetic apparatus 10 is attached by putting the condom 12 on the penis 14 in the usual fashion, with tube 20 extending between the users legs such that syringe 26 may be easily operated. Chamber 24 in the tip 22 of the condom should then be injected with liquid from syringe 26 until a round ball is formed of about a half inch in diameter. This ball is important to prevent tube 20 from rupturing the condom during insertion of the prosthetic device 10 in the users partner.

Once the apparatus 10 has been inserted in the user's partner, additional fluid is injected within chamber 24 until the desired size is achieved. Tube 20 is then removed from the condom by pulling rearwardly on the tube. The restriction caused by rubber bands 18 around condom 12 will seal the fluid within chamber 24 after tube 20 has been removed, as shown in FIG. 1.

All of the various components of the prosthetic apparatus 10 are shown in FIG. 2 and arranged in exploded fashion to demonstrate their correlation. All of the various components may be reused with a new condom 12, thereby eliminating the substantial cost of other prior art prosthetic devices. In addition, any conventional condom 12 having the appropriate wall thickness to retain water under pressure may be utilized in the method of the invention.

Whereas the invention has been shown and described in connection with the preferred embodiment thereof, it will be understood that many modifications, substitutions and additions may be made which are within the intended broad scope of the appended claims. There has therefore been shown and described an improved prosthetic apparatus and method of use which accomplish at least all of the above-stated objects.

I claim:

1. A prosthetic apparatus, comprising:
   a conventional condom having elastic characteristics, and having a closed tip end and an open end;
   restriction means located on said condom between said open and closed ends forming a fluid-sealed chamber in said tip end; and
   fluid under pressure in said fluid-sealed chamber so as to expand said tip end of said condom.

2. A method for forming a prosthetic device, comprising the steps of:
   tightly wrapping an elastic band around a rigid sleeve;
   inserting a first end of a hollow tube into the tip end of a conventional condom and unrolling a length of the condom;
   inserting the tip end of the condom and the tube first end through said sleeve such that the tip end of the condom and the first end of the tube project out of said sleeve;
   moving said elastic band from said sleeve onto the condom and around said tube to form a fluid-sealed chamber in the tip end of the condom, into which said tube communicates;
   removing said sleeve from said condom;
   connecting a source of fluid to the second end of the tube;
   applying the open end of the condom to a body member; and
   injecting fluid from said fluid source through said tube into said chamber so as to expand the tip end of the condom.

3. The method of claim 2, wherein the step of connecting a source of fluid includes the step of providing a syringe filled with liquid and connecting the syringe to the tube's second end.

4. The method of claim 2 wherein the step of injecting fluid includes the step of injecting only a small amount of fluid such that the tip end of the condom forms a substantially round ball, and further includes the steps of:
   inserting the condom and body member into an orifice; and
   injecting additional fluid into said chamber so as to expand the tip end of the condom within the orifice.

5. The method of claim 2, further comprising the step of removing the tube from the condom such that the elastic band forms a fluid-tight chamber in said condom, after the step of injecting fluid.

* * * * *